(12) United States Patent
Turcott et al.

(10) Patent No.: US 6,567,700 B1
(45) Date of Patent: May 20, 2003

(54) IMPLANTABLE CARDIAC STIMULATION DEVICE AND METHOD WHICH OPTIMIZES PACING EFFECTIVENESS

(76) Inventors: Robert Turcott, 938 N. Clark Ave. #40, Mountain View, CA (US) 94040; Kerry Bradley, 3081 Menlo Dr., Glendale, CA (US) 91208; Euljoon Park, 25830 London Pl., Stevenson Ranch, CA (US) 91381

(*) Notice: Subject to any disclaimer, the term of this patent is extended or adjusted under 35 U.S.C. 154(b) by 233 days.

(21) Appl. No.: 09/692,612

(22) Filed: Oct. 19, 2000

(51) Int. Cl.[7] .............................................. A61N 1/368
(52) U.S. Cl. ............................................. 607/9; 607/18
(58) Field of Search .............................. 607/9, 11, 17, 607/18, 19, 23, 27

(56) References Cited

U.S. PATENT DOCUMENTS

| | | | |
|---|---|---|---|
| 5,466,254 A | 11/1995 | Helland | 607/123 |
| 5,487,752 A | 1/1996 | Salo et al. | 607/17 |
| 5,540,727 A * | 7/1996 | Tockman et al. | 607/18 |
| 5,584,867 A * | 12/1996 | Limousin et al. | 607/14 |
| 5,728,140 A | 3/1998 | Salo et al. | 607/9 |
| 5,836,987 A | 11/1998 | Baumann et al. | 607/17 |
| 5,902,324 A | 5/1999 | Thompson et al. | 607/9 |
| 6,101,416 A * | 8/2000 | Sloman | 607/9 |
| 6,377,851 B1 * | 4/2002 | Shieh et al. | 607/9 |
| 6,377,852 B1 * | 4/2002 | Bornzin et al. | 607/9 |

OTHER PUBLICATIONS

Kass, David A., M.D.,et al., "Improved Left Ventricular Mechanics From Acute VDD Pacing in Patients With Dilated Cardiomyopathy and Ventricular Conduction Delay", Circulation, pp 1567–73, (Mar. 1999).

* cited by examiner

Primary Examiner—Willis R. Wolfe

(57) ABSTRACT

An implantable cardiac stimulation device and method optimizes pacing effectiveness of a patient's heart. A pulse generator delivers right and left pacing pulses to corresponding right and left chambers of the heart with a selected pacing delay between the right pacing pulse and the left pacing pulse wherein the selected pacing delay is within a continuum from left chamber pacing only, to simultaneous right and left chamber pacing, and to right chamber pacing only. A sensor senses a parameter, such as ventricular pressure, associated with pacing effectiveness. A control circuit selects the pacing delay, which maximizes the sensed parameter.

24 Claims, 3 Drawing Sheets

IMPLANTABLE CARDIAC STIMULATION DEVICE AND METHOD WHICH OPTIMIZES PACING EFFECTIVENESS

FIELD OF THE INVENTION

The present invention generally relates to an implantable cardiac stimulation device. The present invention more particularly relates to such a device, which automatically adjusts inter-chamber pacing delay to optimize pacing effectiveness.

BACKGROUND OF THE INVENTION

Implantable cardiac stimulation devices are well known in the art. Such devices may include, for example, implantable cardiac pacemakers and defibrillators either alone or combined in a common enclosure. The devices are generally implanted in the pectoral region of the chest beneath the skin of a patient within what is known as a subcutaneous pocket. The implantable devices generally function in association with one or more electrode carrying leads, which are implanted within the heart. The electrodes are positioned within the heart for making electrical contact with their respective heart chamber. Conductors within the leads couple the electrodes to the device to enable the device to deliver the desired therapy.

Traditionally, therapy delivery had been limited to the right side of the heart. However, new lead structures and methods have been proposed and even practiced for also delivering cardiac rhythm management therapy from or to the left heart. These lead structures and methods provide electrode electrical contact with the left atrium and left ventricle of the heart by lead implantation within the coronary sinus of the heart. As is well known, the coronary sinus passes closely adjacent the left atrium, extends into the great vein adjacent the left ventricle, and then continues adjacent the left ventricle towards the apex of the heart.

It has been demonstrated that electrodes placed in the coronary sinus and great vein may be used for left atrial pacing, left ventricular pacing, and cardioversion and defibrillation. These advancements enable implantable cardiac stimulation devices to address the needs of a large patient population from those which would benefit from right heart side pacing alone to those which would benefit from left heart side pacing in conjunction with right heart side pacing (bi-chamber pacing), to those which would benefit from left heart side pacing alone.

For example, the potential of multi-site pacing to improve the hemodynamic status of select patient populations is well established in the research community. One area of active research is in determining the optimal ventricular pacing configuration. For example, the results of one study suggest that optimal results are obtained by pacing on the side of the heart that has the conduction delay, so that left ventricular pacing gives superior performance for patients with a left bundle branch block, while right ventricular pacing yields better results in patients with right bundle branch block. As illustrated by those who conducted this study, the problem is typically couched in terms of pacing mode, so that comparison is made among right ventricular pacing, left ventricular pacing, and simultaneous bi-ventricular pacing. Unfortunately this approach considers only a small subset of the parameter space, and therefore carries the very real risk of missing altogether the optimal pacing configuration.

Multi-site pacing has further challenges. One such challenge is identifying the optimal pacing site. This challenge is complicated by the fact that only a limited region of the left ventricle is accessible for pacing, particularly when access is obtained via the coronary venous system.

An additional challenge in multi-site pacing is that the optimal pacing configuration is dependent on the physiologic state of the patient. In patients with Hypertrophic Obstructive Cardiomyopathy, for example, the degree of obstruction is dependent on posture. Thus, the optimal pacing configuration is likely to change with changes in posture. For example, the optimal configuration for an unsedated, walking patient is likely to be different from what is optimal for a patient who is sedated and supine on the examination or operating table.

The optimal pacing configuration may also change as the patient's myocardial state changes. Myocardial remodeling is associated with the progression or regression of heart failure. Such remodeling may depend on response to therapy, lifestyle changes, and age. As the heart remodels, the optimal sequence of activation may change. For example, in the acute phase of pacemaker implantation, left ventricular pacing may have been optimal for a given patient. Over weeks or months, the heart may remodel such that more synchronous bi-ventricular pacing becomes optimal.

SUMMARY OF THE INVENTION

The present invention provides an implantable cardiac stimulation device and method which optimizes pacing effectiveness by effectively selecting a pacing configuration within a continuum of pacing configurations ranging from right chamber pacing alone, to simultaneous right and left chamber pacing, to left chamber pacing alone. In accordance with the present invention, this is accomplished by selecting an inter-chamber pacing delay ranging from a delay which captures only a right chamber of the heart, to no delay for synchronous bi-chamber pacing, to a delay which captures only a left chamber of the heart responsive to a sensed parameter associated with pacing effectiveness.

In accordance with the present invention, a pulse generator delivers right and left pacing pulses to corresponding respective right and left chambers of the heart. The corresponding right and left chambers may be, for example, the right and left ventricles or the right and left atria. The right and left pacing pulses are delivered with a selected pacing delay therebetween which delay is within a continuum from left chamber pacing alone, to simultaneous right and left chamber pacing, to right chamber pacing alone. A sensor, such as a ventricular pressure sensor, which senses ventricular pressure associated with hemodynamic output, provides a pulse amplitude. A control circuit selects the pacing delay which provides the maximum pulse amplitude. In this manner, a pacing delay is selected which optimizes the mechanical efficiency of the heart.

In accordance with a preferred embodiment, the control circuit includes a processor. The processor is programmed to initiate a pacing delay selection and to cause the pulse generator to vary the pacing delay with successive cardiac cycles until a maximum in the sensed parameter is obtained. The processor may continuously initiate the pacing delay selection or may initiate pacing delay selection at spaced apart times or when the patient changes posture.

The present invention thus enables bi-chamber pacing to be amenable to continuous hemodynamic performance maximization even as physiologic state changes. It further obviates the need for optimized electrode placement as, for example, a left ventricular pacing site, by compensating for a sub-optimal electrode placement.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
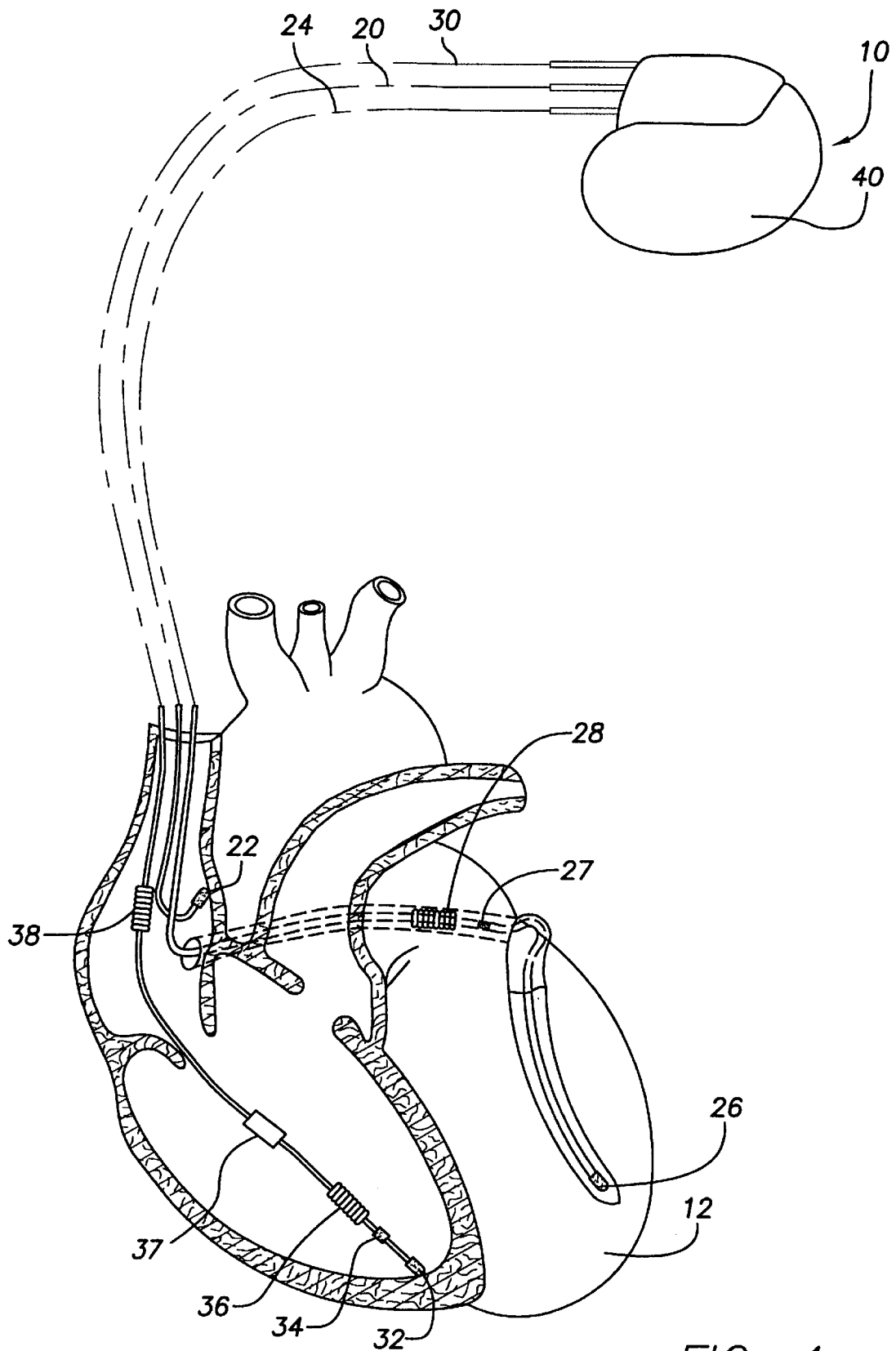
FIG. 1 is a simplified diagram illustrating an implantable stimulation device in electrical communication with at least three leads implanted into a patient's heart for delivering multi-chamber stimulation and shock therapy and which embodies the present invention.

As shown in FIG. 1, there is a stimulation device 10 in electrical communication with a patient's heart 12 by way of three leads, 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, titled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

The lead 30 further includes a pressure sensor 37, which senses ventricular pressure. Ventricular pressure is a parameter associated with or related to hemodynamic output of the heart and hence provides a reliable indication of pacing effectiveness or mechanical efficiency of the heart. As will be seen subsequently, the ventricular pressure is used to select an optimum pacing delay. The output of the sensor 37 is a pulse amplitude following each stimulation. The pacing delay producing the maximum is selected to maximize the pulse amplitude.

Figure 2:
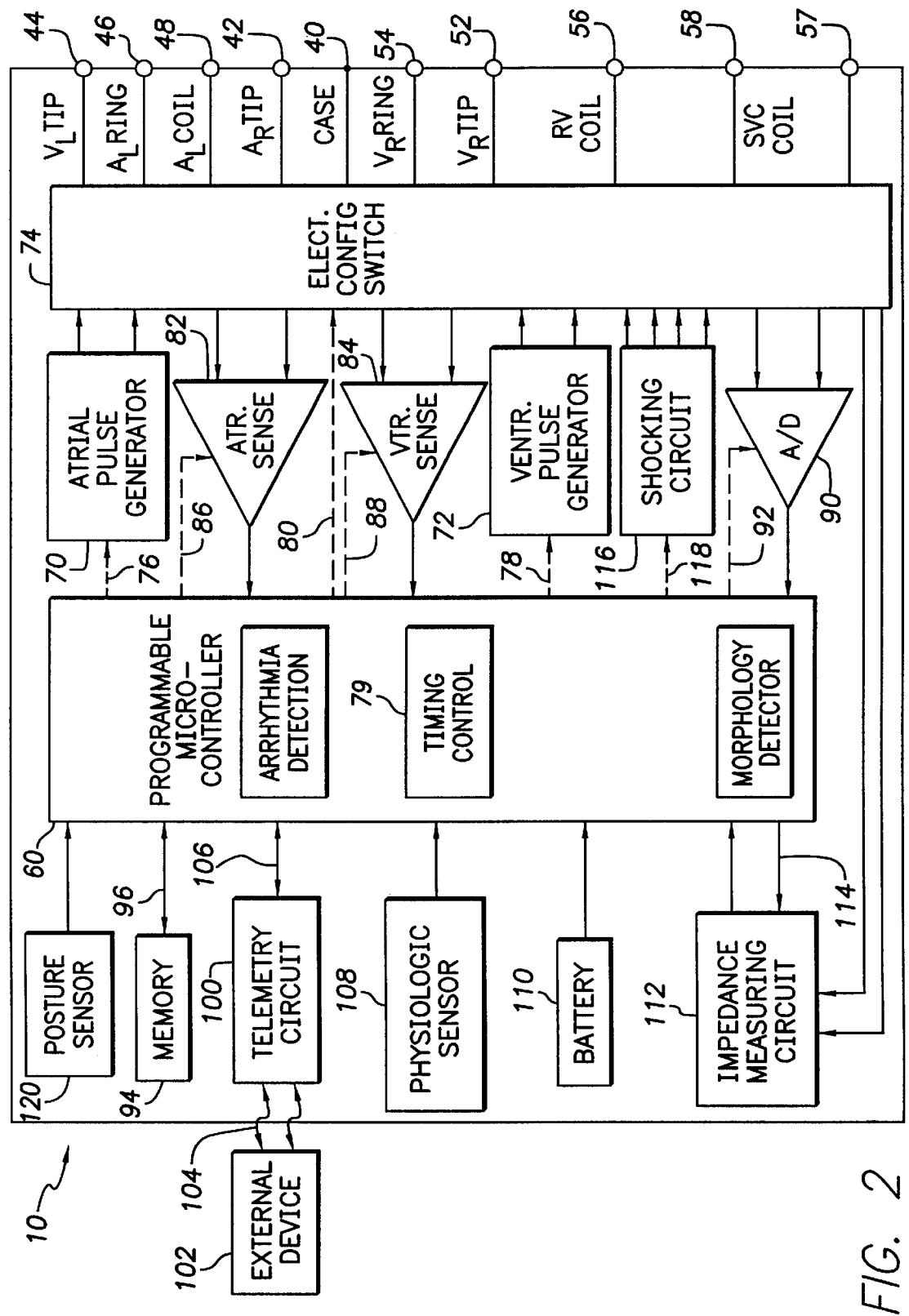
FIG. 2 is a functional block diagram of the device of FIG. 1 illustrating the basic elements for providing cardioversion, defibrillation and pacing stimulation in four chambers of the heart and for optimizing pacing therapy in accordance with a preferred embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing circuitry which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

The switch bank 74 also selectively couples a pressure sensor terminal 57 to the microcontroller. The terminal 57 is coupled to the pressure sensor 37 of lead 30 (FIG. 1). This enables the microcontroller 60 to read the pulse amplitude from the pressure sensor 37 following each stimulation during a pacing delay selection.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (AND) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter, which corresponds to the exercise state of the patient. The type of sensor used is not critical to the present invention and is shown only for completeness.

The stimulation device additionally includes a battery 110, which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 employs lithium/silver vanadium oxide batteries, as is true for most (if not all) such devices to date.

The device 10 further includes a posture sensor 120. The posture sensor detects the posture of the patient between a fully upright position and a supine position. To that end, the sensor 120 may include accelerometers, which detect acceleration in three mutually transverse directions. The raw signals from the sensor 120 are provided to the microcontroller 60, which may generate two different control signals. A first control signal may be a logical "1" if the patient is in an upright position and a logical "0" if the patient is in a supine position. A second control signal may be a multiple-bit binary fractional factor between 0 and 1 representing the posture of the patient. For example, the fractional factor may vary from 0, representing the patient in a supine position, to 1, representing the patient in a fully upright position. One such posture sensor is fully described in copending U.S. application Ser. No. 09/457,451, filed Dec. 8, 1999, titled "AC/DC Multi Axis Accelerometer for Determining Patient Activity and Body Position," which application is owned by the assignee of the present invention and incorporated herein in its entirety by reference.

The posture sensor 120 may be used to initiate a pacing delay selection. When the posture sensor indicates that the patient's posture has changed, the microcontroller may then initiate another pacing delay selection.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 by a control signal 114. The impedance measuring circuit 112 is not critical to the present invention and is shown for only completeness.

It is the primary function of the device 10 to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
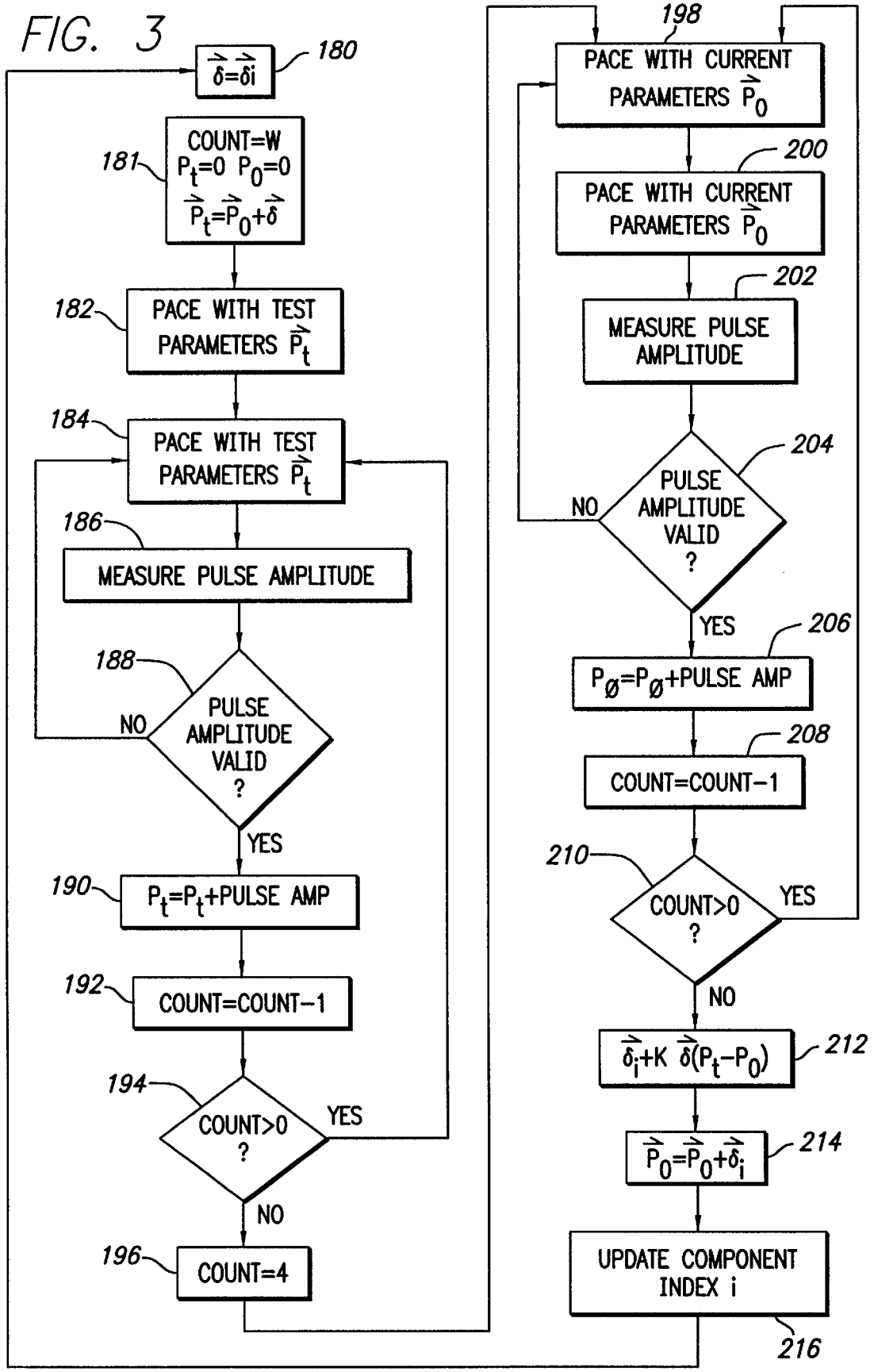
FIG. 3 is a flow chart describing the operation of the device of FIGS. 1 and 2 during pacing therapy optimization in accordance with a preferred embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Before the flow chart of FIG. 3 is described in detail, a brief summary of the pacing delay selection may prove helpful. The pacing delay selection of the present invention is based upon the realization that between the continuum about zero delay, at which both the right and left chambers, for example the ventricles, are paced simultaneously, there is a maximum of pacing effectiveness. At one end of the continuum is the left ventricular pacing only, wherein the left ventricle is stimulated first to capture the left ventricle and then the right ventricle is paced, after a large negative delay, when the right ventricle is refractory and not captured. At the extreme other end of the continuum is right ventricular pacing only where in the right ventricle is paced to capture the right ventricle and then, after a large positive delay, when the left ventricle is refractory, the left ventricle is paced and not captured. Between the extreme ends of this continuum is a pacing delay, either positive or negative, which yields maximum pacing effectiveness and a maximum pulse amplitude from the pressure sensor 37.

The invention therefore contemplates commencing pacing in the left chamber(s) of the heart, followed by pacing in the right chamber(s) of the heart, subject to a time delay from zero seconds to a preselected maximum delay value, as well as commencing pacing in the right chamber(s) of the heart, followed by pacing in the left chamber(s) of the heart, subject to a time delay from zero seconds to a preselected maximum delay value. Obviously, a zero time delay manifests in simultaneous pacing in both right and left chamber (s).

When a pacing delay selection is initiated by the microcontroller, the left and right ventricles are paced during successive cardiac cycles with varying pacing delay. When the pulse amplitude from the pressure sensor is maximum, indicating maximum effectiveness, mechanical efficiency, or hemodynamic output, the pacing delay causing the maximum pulse amplitude is selected by the microcontroller 60 and thereafter used until the next pacing delay selection. The next pacing delay selection may be initiated as programmed, either at another spaced apart time, continuously, or responsive to a change in the posture of the patient. As will be appreciated by those skilled in the art, the foregoing applies equally as well as the atria wherein the corresponding right and left chambers would then be the right atrium and the left atrium.

In accordance with this preferred embodiment, the pulse amplitude can be obtained in any of a variety of ways. For example, although ventricular pressure determined by an intracavitary pressure transducer is preferred, vascular plethysmography can be used to obtain a measure of arterial pulse amplitude. Alternatively, heart sounds can be used to obtain a measure of the strength of cardiac contraction. Other measures of hemodynamic function are possible, including ultrasound to detect changes in the diameter of the aorta or other vessels during the cardiac cycle, Doppler ultrasound to detect the blood flow through the arteries, cardiac motion detected by an accelerometer, ventricular volume detected by intracardiac or extracardiac impedance plethysmography, and mechanical distention of the arteries measured, for example, using a strain gauge, accelerometer, or pressure transducer. The term 'pulse amplitude' is thus intended to be used in the generic sense as some measure of mechanical pumping efficacy of the heart and is used to refer to any measure of mechanical cardiac hemodynamic function generated on a beat-by-beat basis. Arterial pulse amplitudes which are pulse amplitude measures derived from the increased pressure and distension of the arterial vasculature that results from a systolic pulse may alternatively be used.

Measures of arterial pulse amplitude include, for example, optical vascular plethysmography, intra- or extra-arterial pressure transduction, and ultrasound sensing.

A preferred embodiment of a process for performing pace-parameter optimization using a hemodynamic or pressure sensor is presented in FIG. 3. In this process the pacing parameters are represented with a vector notion $\vec{p}$. In the preferred embodiment this vector represents the value of the RA-RV delay (AV delay) and the RV-LV delay, so that it has two components and optimization takes place over a two-dimensional space. The pacing rate is determined by a conventional rate-responsive pacing algorithm. The current set of pacing parameters is represented with the notation $\vec{p}_0$, and the set of test parameters is represented with the notation $\vec{p}_t$.

In the preferred embodiment, one component of the vector is modified, tested, and updated on each pass through the process. For example, the current parameters might be $\vec{p}_0 = [100, 30]$, where the first component represents the AV delay and the second component represents the RV-LV delay, both in msec. The test vector is $\vec{p}_t = \vec{p}_0 + \vec{\delta}$, where $\vec{\delta} = [0.10]$. Thus the test parameters are identical to the current parameters but with an RV-LV delay that is longer by 10 msec. The hemodynamic responses, $p_t$ and $p_0$, respectively, of $\vec{p}_t$ and $\vec{p}_0$ are obtained and $\vec{p}_0$ is updated depending on the responses. Specifically, the component tested, in this example the RV-LV delay, is changed by an amount proportional to the test difference and proportional to the difference between the hemodynamic responses, so that $\vec{p}_0 \leftarrow \vec{p}_0 + k^* \vec{\delta}^* (p_t - p_0)$, where k is a predetermined constant scale factor, $p_t$ represents the pulse amplitude associated with pacing using $\vec{p}_t$, $p_0$ is the pulse amplitude associated with pacing using $\vec{p}_0$, and ← denotes replacement. The amount by which $\vec{p}_0$ is updated is assigned to $\delta_i$, $\delta_i = k^* \vec{\delta}^* (p_t - p_a)$, and stored in memory for the next iteration that component i, the AV delay in this case, is updated.

Proceeding in detail through the preferred embodiment presented in FIG. 3, at step 180 the increment vector $\vec{\delta}$ is assigned the value $\vec{\delta}_i$, which is either the default increment setting or contains a value that was stored during a previous pass. The subscript i indicates that it is specific for the component presently being tested. At step 181 count is initialized to 4, and the variables $p_t$ and $p_0$, which represent the hemodynamic responses of the test and current parameter settings, respectively, are set to zero. In addition, the test parameter setting is assigned the value $\vec{p}_t = \vec{p}_0 + \vec{\delta}$. A first pacing pulse is delivered using the test parameters $\vec{p}_t$ at step 182. The hemodynamic result of this pace set is not recorded since it is potentially influenced by preload conditions that are determined from the parameters that defined the previous paced beat. Another pace set is delivered at step 184 using $\vec{p}_t$. The pulse amplitude is determined at step 186.

A test for the validity of the pulse amplitude is made at step 188. If the pulse amplitude is not valid, the process returns to step 184 without the variables being modified. If the pulse amplitude is valid then $p_t$ is incremented by the measured pulse amplitude, step 190, and the count is decremented, step 192. If the count is greater than zero, step 194, the process returns to step 184, otherwise, the count is set to 4 at step 196, and a first pace set is delivered using the current parameters $\vec{p}_0$ at step 198. Hemodynamic measurements are not made following this first beat because they could be influenced by preload conditions generated by the previous pace set, which used the test parameters $\vec{p}_t$. Another pace set is delivered using the current parameters $\vec{p}_0$ at step 200. Following this pace set the pulse amplitude is measured at step 202. If the pulse amplitude is not valid, tested at step 204, then the process returns to step 200 without modification to the variables. If the pulse amplitude is valid, then $p_0$ is incremented by the pulse amplitude at step 206, and the count is decremented at step 208. The process returns to step 200 if the count is above zero at step 210, otherwise, the change to the current parameter set $\vec{\delta}_i$ is calculated at step 212 and used to update the current parameter set $\vec{p}_0$ at step 214. It is retained in memory for later use on successive passes. Finally, the component index i is updated at step 216, and control returns to step 180 for another pass through the algorithm.

This algorithm is advantageous in that the step size $\vec{\delta}_i$ is adaptive. It is largest in those regions of the optimization space that are far from the optimal parameter settings, where $p_0$ and $p_t$ are substantially different in magnitude, and it is smallest in those regions of the space that are close to the optimal settings, in which $p_0$ and $p_t$ are similar in magnitude so their difference is small. Thus the point representing the parameter settings speeds rapidly through the optimization space to the optimum. Furthermore, the trial step size $\vec{\delta}_i$ is taken to be the same as the last update. Both these attributes speed convergence to the optimal parameter settings and therefore allow rapid, dynamic adjustment of parameters, so that even changes in body position from supine to standing can be rapidly accommodated.

In the preferred embodiment the process is run continuously. Alternate embodiments include performing the pacing delay selection intermittently, such as at periodic intervals or after a change of posture is detected. In still another alternate embodiment the scale factor k is slowly decreased so that the pacing parameters converge to a stable point. This embodiment is particularly useful for intermittent optimization.

In accordance with alternate embodiments, the newly updated pacing parameters may be used to deliver some predetermined number of paced beats before a new parameter set is tested. This decreases the rate of convergence but allows the patient's hemodynamics to stabilize somewhat at the new pacing set.

In accordance with alternate embodiments, a different number of pacing parameters may be optimized. For example, if four-chamber pacing is used, the RA-LA, RA-RV, and RA-LV intervals may also be optimized. In this case $\vec{p}$ is a three dimensional vector and optimization is performed over a three dimensional space. In general, the number of dimensions of $\vec{p}$ is equal to the number of intervals to be optimized.

In other embodiments, more than one electrode is used to stimulate a given chamber, and the timing pulses delivered through these electrodes are optimized the same way as the case of one electrode per chamber.

In still other embodiments all components are tested and modified simultaneously, for example, using a simplex method.

In further embodiments, an exhaustive search of the parameter space is performed, in which all combinations of intervals are tested, and the combination that results in the optimal hemodynamic performance, as assessed by the sensor, is retained and used.

In yet other embodiments, an evolutionary algorithm is used, in which a population of points in parameter space is maintained. At each iteration, the delays represented by each point are used and the resulting hemodynamic performance is recorded. The best-performing points are retained, and the worst-performing points are replaced by randomly modified versions of the retained points.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device which optimizes pacing effectiveness of a patient's heart comprising:
    a pulse generator configured to:
        deliver right and left pacing pulses to corresponding respective right and left chambers of the heart with a selected pacing delay between the delivery of the right pacing pulse and the delivery of the left pacing pulse within a continuum from left chamber pacing alone, to the delayed pacing between right chamber and left chamber, to simultaneous right chamber and left chamber pacing, and to right chamber pacing alone;
    a sensor that senses a parameter associated with pacing effectiveness; and
    a control circuit that selects the pacing delay which maximizes the sensed parameter, wherein the control circuit includes a processor programmed to cause the pulse generator to deliver the right and left pacing pulses with varying pacing delays until a maximum of the parameter is sensed by the sensor.

2. The device of claim 1 wherein the sensor provides a pulse amplitude indicative of the sensed parameter and wherein the control circuit responds to the pulse amplitude in selecting the pacing delay.

3. An implantable cardiac stimulation device for optimizing pacing therapy delivered to a patients heart, the device comprising:
    stimulation means for applying right and left stimulation pulses to corresponding respective right and left chambers of the heart, the stimulation pulses having a selected relative delay in a continuous range of relative delays from left chamber stimulation only, to synchronous right and left chamber stimulation, and to right chamber stimulation only;
    sensing means for sensing a parameter associated with pacing therapy effectiveness following each application of the right and left stimulation pulses; and
    control means responsive to the sensing means for selecting the relative delay corresponding to a maximum value of the sensed parameter, wherein the control means includes means for causing the stimulation means to apply the right and left stimulation pulses with varying relative delays until a maximum of the parameter is sensed by the sensing means.

4. The device of claim 3 wherein the sensing means provides a pulse amplitude indicative of the sensed parameter and wherein the control means is responsive to the pulse amplitude for selecting the relative delay.

5. In an implantable cardiac stimulation device, a method of optimizing pacing therapy provided to a patients heart, the method comprising:

applying right and left stimulation pulses to corresponding respective right and left chambers of the heart with a selected delay between application of the right and left simulation pulses within a continuum from left chamber capture only, to simultaneous right and left chamber stimulation, and to right chamber capture only;

sensing a parameter associated with pacing effectiveness;

selecting the selected delay responsive to the sensed parameter being a maximum;

wherein the apply step includes applying the right and left stimulation pulses with varying delays until a maximum of the parameter is sensed.

6. The method of claim 5 wherein the sensing step includes providing a pulse amplitude indicative of the sensed parameter and wherein the selecting step is performed when the pulse amplitude is a maximum.

7. An implantable cardiac stimulation device which optimizes pacing effectiveness of a patient's heart comprising:

a pulse generator configured to:

deliver right and left pacing pulses to corresponding respective right and left chambers of the heart with a selected pacing delay between the delivery of the right pacing pulse and the delivery of the left pacing pulse within a continuum from left chamber pacing alone, to the delayed pacing between right chamber and left chamber, to simultaneous right chamber and left chamber pacing, and to right chamber pacing alone;

a sensor that senses a parameter associated with pacing effectiveness; and a control circuit that selects the pacing delay which maximizes the sensed parameter, wherein the control circuit includes a processor programmed to initiate pacing delay selection at spaced apart times.

8. The device of claim 7 further including a posture sensor that senses posture of the patient and wherein the processor is programmed to initiate pacing delay selection responsive to a change in posture of the patient.

9. The device of claim 7 wherein the corresponding respective right and left chambers are the right ventricle and the left ventricle respectively and wherein the pulse generator delivers the right and left pacing pulses to the right ventricle and left ventricle respectively.

10. The device of claim 7 wherein the corresponding respective right and left chambers are the right atria and the left atria respectively and wherein the pulse generator delivers the right and left pacing stimulation pulses to the right atrium and left atrium, respectively.

11. The device of claim 7 wherein the sensed parameter is mechanical efficiency of the heart.

12. The device of claim 11 wherein the mechanical efficiency sensed parameter is ventricular pressure and wherein the sensor includes a pressure sensor.

13. An implantable cardiac stimulation device for optimizing pacing therapy delivered to a patients heart, the device comprising:

stimulation means for applying right and left stimulation pulses to corresponding respective right and left chambers of the heart, the stimulation pulses having a selected relative delay in a continuous range of relative delays from left chamber stimulation only, to synchronous right and left chamber stimulation, and to right chamber stimulation only;

sensing means for sensing a parameter associated with pacing therapy effectiveness following each application of the right and left stimulation pulses; and control means responsive to the sensing means for selecting the relative delay corresponding to a maximum value of the sensed parameter, wherein the circuit means includes initiating means for initiating a delay selection at spaced apart times.

14. The device of claim 13 further including a posture sensing means for sensing posture of the patient and wherein the initiating means is responsive to the posture sensing means for initiating a delay selection responsive to a change in posture of the patient.

15. The device of claim 13 wherein the corresponding respective right and left chambers are the right ventricle and the left ventricle respectively and wherein the stimulation means is configured to apply the right and left stimulation pulses to the right ventricle and left ventricle respectively.

16. The device of claim 13 wherein the corresponding respective right and left chambers are the right atria and the left atria respectively and wherein the stimulation means is configured to apply the right and left stimulation pulses to the right atria and left atria respectively.

17. The device of claim 13 wherein the sensed parameter is mechanical efficiency of the heart.

18. The device of claim 17 wherein the mechanical efficiency sensed parameter is ventricular pressure and wherein the sensing means includes a pressure sensor.

19. In an implantable cardiac stimulation device, a method of optimizing pacing therapy provided to a patient's heart, the method comprising:

applying right and left stimulation pulses to corresponding respective right and left chambers of the heart with a selected delay between application of the right and left stimulation pulses within a continuum from left chamber capture only, to simultaneous right and left chamber stimulation, and to right chamber capture only;

sensing a parameter associated with pacing effectiveness;

selecting the selected delay responsive to the sensed parameter being a maximum; and initiating a delay selection at spaced apart times.

20. The method of claim 19 including the further steps of sensing posture of the patient and initiating a delay selection responsive to a change in posture of the patient.

21. The method of claim 19 wherein the corresponding respective right and left chambers are the right ventricle and the left ventricle respectively and wherein the applying step includes applying stimulation pulses to the right ventricle and left ventricle.

22. The method of claim 19 wherein the corresponding respective right and left chambers are the right atria and the left atria respectively and wherein the applying step includes applying stimulation pulses to the right atria and left atria.

23. The method of claim 19 wherein the sensed parameter is mechanical efficiency of the heart.

24. The method of claim 23 wherein the mechanical efficiency sensed parameter is ventricular pressure and wherein the sensing step includes sensing ventricular pressure.

\* \* \* \* \*